United States Patent [19]

Pan Ping et al.

[11] Patent Number: 5,305,815
[45] Date of Patent: Apr. 26, 1994

[54] METHOD AND APPARATUS FOR PREDICTING MICROSTRUCTURE OF CAST IRON

[75] Inventors: Zhu Pan Ping; Reginald W. Smith, both of Kingston, Canada

[73] Assignee: Queen's University, Kingston, Canada

[21] Appl. No.: 968,879

[22] Filed: Oct. 30, 1992

[51] Int. Cl.⁵ .......................... B22D 2/00; G01N 1/10; G01K 13/12
[52] U.S. Cl. ................. 164/4.1; 249/DIG. 4; 73/864.58; 73/864.53; 73/DIG. 9; 374/139; 374/157
[58] Field of Search .......... 164/4.1, 150, 154; 75/377, 382; 266/79, 88; 249/DIG. 4; 73/864.58, 864.53, DIG. 9; 374/139, 157, 179

[56] References Cited

U.S. PATENT DOCUMENTS 4,059,996  11/1977  Cure ..................................... 164/4.1

*Primary Examiner*—Kuang Y. Lin
*Attorney, Agent, or Firm*—Richard J. Hicks

[57] ABSTRACT

A method and apparatus for predicting nodularity of a hypo or hyper eutectic cast iron melt during casting is described. The method is particularly useful for NiMg-treated melts but can also be used for rare earth treated melts. A small sample of the melt is poured into a sample cup to which up to 0.025% wt bismuth is added and a cooling curve is produced during cooling. In a NiMg treated melt, a $\Delta T$ (TER−TEU) of at least 9° C. indicates good nodularity. In an RE treated melt, a $\Delta T$ of less than 6° C. at a TER/TEU of 1140° C. also indicates good nodularity will be observed upon the solidification of the melt.

11 Claims, 3 Drawing Sheets

METHOD AND APPARATUS FOR PREDICTING MICROSTRUCTURE OF CAST IRON

FIELD OF INVENTION

This invention relates to the microstructure of cast iron and more particularly to a method and apparatus for predicting graphite morphology of cast irons treated with nodularizing agents.

BACKGROUND OF INVENTION

Cast irons containing nodular graphite are well known in the art (Morrogh et al, J.I.S.I. 1970 (1948) 306) and many attempts have been made to predict the microstructure of cast iron, and in particular the nodularity of the graphite, by thermal analysis of test samples of iron melts. Backerud et al (The Metallurgy of Cast Iron, Georgi Publishing Co., Switzerland (1975) 625-637) studied Mg-treated nodular graphite iron by thermal analysis and found that the cooling curve for a vermicular/compacted graphite (CG) iron during the eutectic phase transformation falls between that of flake and nodular irons but that the eutectic recalescence for vermicular iron may exceed that of a flake or nodular iron.

Stefanescu et al, (Trans. AFS 90 (1982) 333-348) however, reported that the cooling curve of a vermicular/CG iron does not really lie between those of flake and nodular iron but rather crosses these curves several times. In these later studies, however, a rare earth or 0.5% cerium containing Mg Fe Si alloy was used as a nodulizer.

Loper et al (Metallurgy of Cast Iron, Proceedings of St. Saphorin Conference, Georgi Publishing Co. 1975, p. 640-657) studied the effect of NiMg treatment with and without postinoculation and reported that no eutectic recalescence occurred for a hypoeutectic nodular iron treated with NiMg without postinoculation, while a small eutectic recalescence was observed for hypereutectic nodular iron with the same treatment. After post-inoculation, the overall eutectic temperature was raised but the eutectic temperature was decreased in a continuous manner for hypereutectic nodular iron. Monroe and Bates (Trans AFS, 90 (1982) 307-311) showed that solidification of Mg-treated irons at a eutectic temperature of about 1150° C. indicates inadequate Mg treatment. Eutectic solidification at about 1132° C. can be considered to reflect spheroidal graphite (SG) growth, while lower temperatures are indicative of massive carbide formation.

While it is known that the primary role of cerium in cast iron is to desulphurize the melt and then inhibit carbide decomposition, it is believed to have a secondary role in neutralizing "subversive" elements, such as bismuth, lead, and antimony present in the melt. Subversive elements all have an effect on graphite morphology but their effect on the cooling curves for nodular cast iron are unknown.

It will be appreciated, therefore, that both magnesium and cerium and/or trace elements have an effect on graphite morphology but the prior art teachings make it difficult to predict those effects accurately. It would be extremely useful to the founder to be able to predict the graphite morphology of a given melt of nodular iron before the melt is actually cast so that adjustments to composition etc. can be made so as to improve the quality of the final product.

There is, therefore, a need for a method and apparatus for predicting graphite morphology of a nodular iron before casting thereof.

OBJECT OF INVENTION

It is, therefore, an object of the present invention to provide a method for predicting the nodularity of cast iron before the casting thereof.

Another object is to provide an apparatus for use in predicting subsequent nodularity of a cast iron melt.

BRIEF DESCRIPTION OF INVENTION

By one aspect of this invention there is provided a method for predicting the nodularity of a cast iron melt treated with a nodularizing agent, comprising:
(a) providing a ceramic test cup which includes bismuth in an amount up to about 0.025% by weight of a sample of said melt;
(b) introducing said sample into said cup;
(c) measuring the temperature of said sample at selected intervals of time so as to produce a cooling curve for said sample; and
(d) determining the difference ($\Delta T$) between a eutectic recalescence temperature (TER) and a eutectic undercooling temperature (TEU) from said cooling curve, and predicting a degree of nodularity therefrom.

By another aspect of this invention there is provided an apparatus for measuring a eutectic recalescence temperature (TER) and a eutectic undercooling temperature (TEU) in a cooling cast iron melt which has been treated with a nodularizing agent, comprising test cup means to receive a liquid sample of said melt; said test cup means including bismuth in an amount up to about 0.025% by weight of said sample and thermocouple means; and means connected to said thermocouple means to read and record temperature in said cooling sample at selected intervals of time so as to produce a cooling rate curve for said sample, including said TER and TEU, the difference between which provides a measure of nodularity in said cast iron melt upon solidification.

DETAILED DESCRIPTION OF PREFERRED EMBODIMENTS

Figure 6:
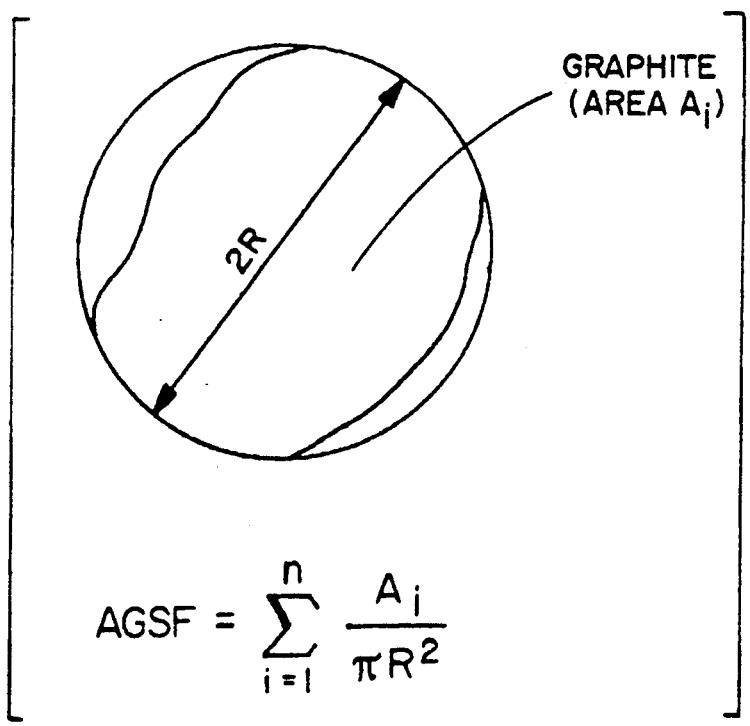
FIG. 6 is a graph illustrating a method for determining an average graphite shape factor (AGSF) for cast iron.

Insufficient residual magnesium is one of the principal reasons that a nodulizer-treated iron melt does not result in fully nodularized graphite. This may be caused by either insufficient addition of nodulizer or excessive consumption caused by high sulphur or subverse elements contained in the melt. When the residual magnesium content is above about 0.04% wt, the graphite structure will be in the nodular form. This form is characterized by an average graphite shape factor (AGSF), as defined in FIG. 6, greater than 0.7. When the residual magnesium range is 0.04–0.035% wt, the graphite structure will range from irregular (AGSF 0.65–0.5) to compacted (AGSF 0.5–0.35); with less than 0.025% wt residual magnesium the graphite will be substantially in flake form (AGSF<0.35). While the difference ($\Delta T$) between the eutectic recalescence temperature (TER) and the eutectic undercooling temperature (TEU) tends to increase as nodularity decreases, there is, in fact, no direct relationship between $\Delta T$ and AGSF for either hypoeutectic or eutectic nodular cast iron treated with a NiMg nodulizer master alloy. The TEU for NiMg-treated melt is usually above 1155° C. and the TER is about 1158°–1160° C.

It has now been found, however, that when increasing amounts of a "subversive" element such as lead, or bismuth are added to a substantially eutectic melt treated with a NiMg nodularizing agent (containing 15.4% Mg 0.02% C 0.05% Co, 0.26 Fe 0.23% Si balance Ni), the AGSF fails from about 0.7 to about 0.2 (FIG. 1), even though the residual Mg level is above 0.04% wt, i.e. the melt would have solidified as fully nodular iron if the subversive elements were not added. Additions of antimony or titanium have very little or no effect and are shown in FIG. 1 for comparison purposes.

Figure 1:
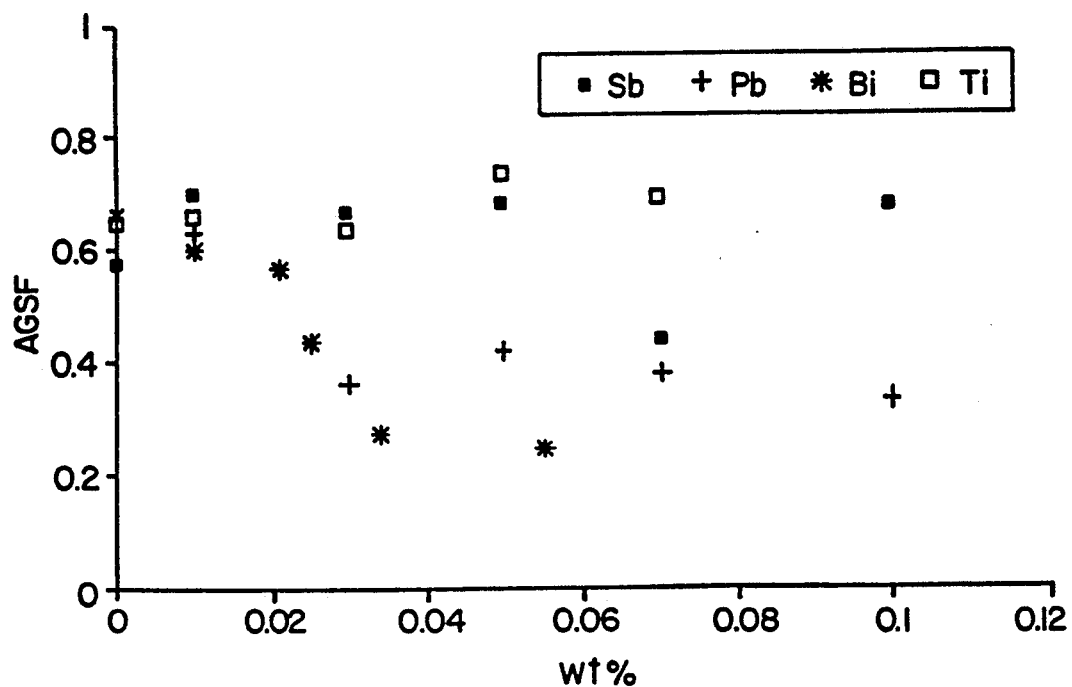
FIG. 1 is a graph illustrating AGSF for a hypoeutectic cast iron with varying additions of Ti, Sb, Pb and Bi.
Figure 2:
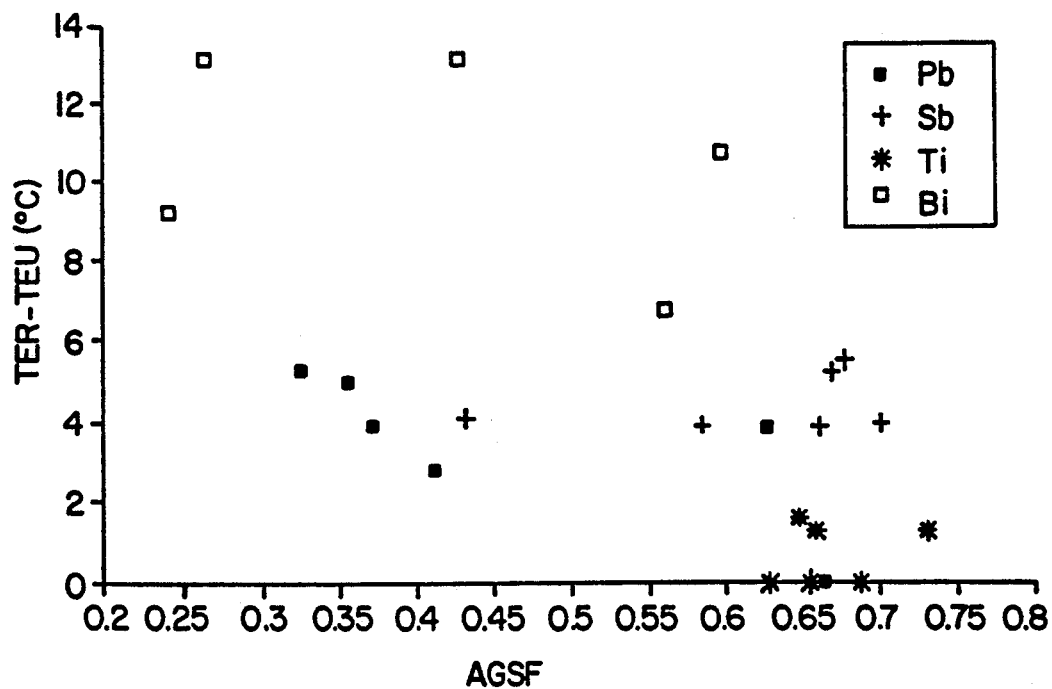
FIG. 2 is a graph illustrating $\Delta T$ versus AGSF for irons of FIG. 1.

Thermal analysis was carried out on the melts illustrated in FIG. 1 containing 3.9% C, 1.384% Si, 0.01% Mn 0.020% P and 0.007% S balance Fe using a ceramic test cup 4.25 cm high and 3.8 cm square at the top and 3.2 cm square at the bottom (manufactured by Electro-Nite), having a horizontally positioned K-type thermocouple mounted therein. The cooling rate of a 360–400 g sample from a casting temperature of 1350°–1400° C. to a temperature below the eutectic temperature was measured over a 4 minute period, and cooling curves were generated in accordance with conventional procedures. From these data and metallographic examination of the cast samples to determine the AGSF value, FIG. 2 was generated, which shows that a bismuth addition generates a much higher recalescence ($\Delta T$) of >10° C. than other trace additions. It has been noted that bismuth decreases both TEU (~1132° C.) and TER (>1140° C.) but decreases TEU much more significantly than TER, which allows the large recalescence ($\Delta T$=TER−TEU) to appear. Antimony or lead additions produce a $\Delta T$ of 4°–5° C. i.e. much smaller than bismuth. titanium has little or no recalescence effect.

Figure 3:
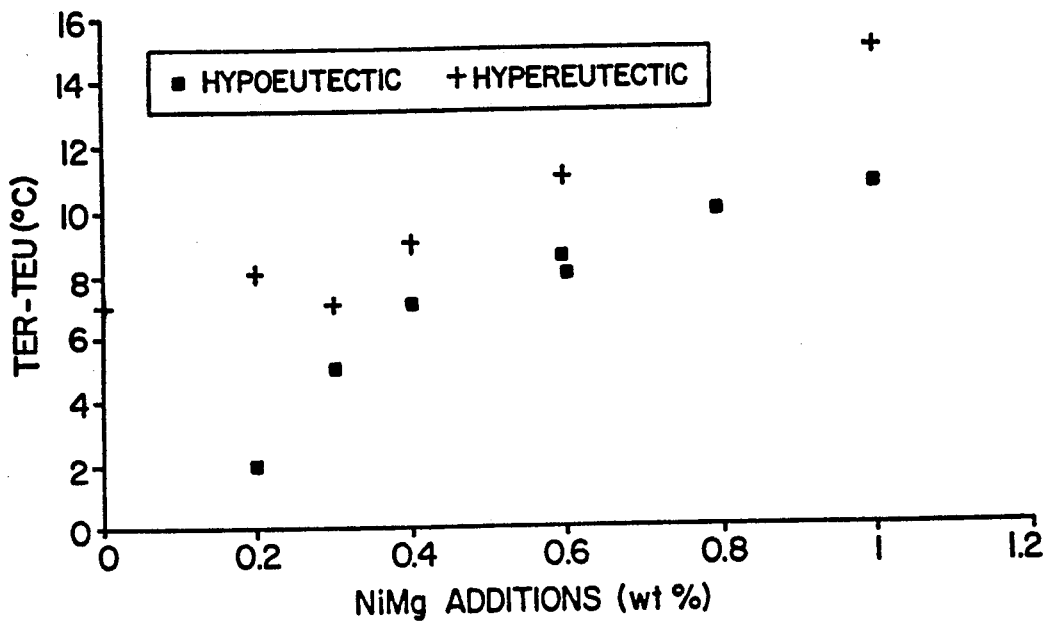
FIG. 3 is a graph illustrating the relationship between NiMg additions and $\Delta T$ in hypo and hyper eutectic cast irons treated in a Bi-added cup.

Based on the above findings it is apparent that the addition of a small amount (0.005–0.025% wt) of bismuth to a standard thermal analysis cup and then conducting a standard thermal analysis will provide an excellent prediction of the nodularity of the cast iron. FIG. 3 shows the relationship between NiMg additions and the recalescence for both hypo and hyper eutectic nodular cast iron with 0.01% wt Bi added to the cup. A $\Delta T$ of 9° C. or higher indicates that a NiMg-treated melt will solidify as fully nodular graphite iron.

Figure 4:
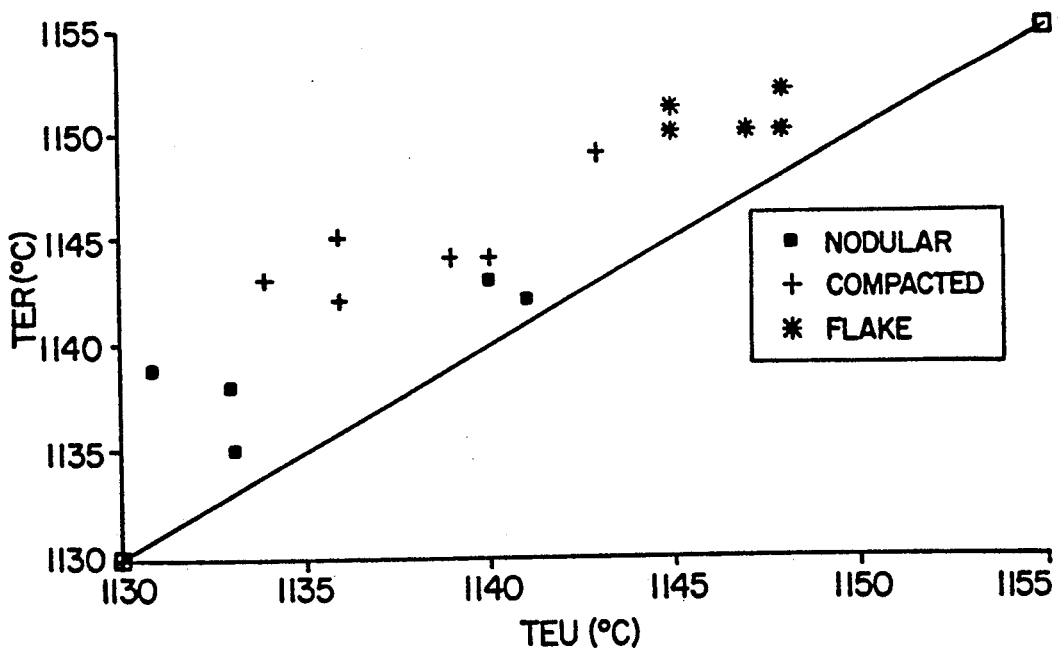
FIG. 4 is a graph illustrating TEU and TER for cast iron with different graphite structures, treated with rare earth containing nodulizers.
Figure 5:
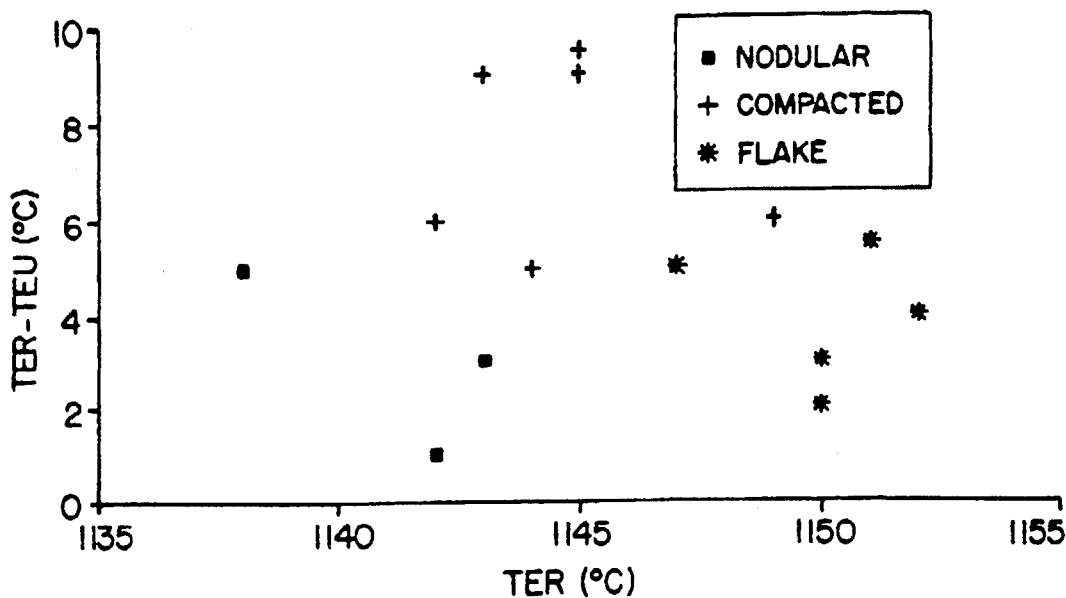
FIG. 5 is a graph illustrating TER and $\Delta T$ for cast iron with different structures, treated with rare earth-containing nodulizers.

The invention has been described thus far with reference to NiMg treated irons, but it will be appreciated that nodular irons may also be made using rare earth (RE)-containing nodulizers, particularly rare earths containing cerium. Bismuth is largely consumed by RE's in the nodulizer and consequently little recalescence is observed. However the TEU for an RE-treated iron is about 1140° C. and at this temperature a $\Delta T$ of up to about 6° C. indicates a nodular iron (FIGS. 4 and 5). If the $\Delta T$ is greater than 6° C. a change from nodular to vermicular during solidification can be expected. Therefore, the Bi-cup finds a use in assessing nodularity of an RE-treated iron if recalescence is considered in conjunction with the absolute eutectic temperature.

We claim:

1. A method for predicting nodularity of a cast iron melt treated with a nodularizing agent, comprising:
   (a) providing a ceramic test cup which includes bismuth in an amount in the range 0.005–0.025% by wt of a sample of said melt;
   (b) introducing said sample into said cup;
   (c) measuring the temperature of said sample at selected intervals of time so as to produce a cooling curve for said sample; and
   (d) determining the difference ($\Delta T$) between a eutectic recalescence temperature (TER) and a eutectic undercooling temperature (TEU) for said cooling curve, and predicting a degree of nodularity therefrom.

2. A method as claimed in claim 1 wherein said nodularizing agent is a nickel-magnesium alloy.

3. A method as claimed in claim 2 wherein $\Delta T$ is at least 9° C. and said cast iron solidifies with a nodularized graphite structure.

4. A method as claimed in claim 1 wherein said nodularizing agent is a rare-earth containing alloy.

5. A method as claimed in claim 4 wherein $\Delta T$ is not more than 6° C. at a TER/TEU of 1140° C. and said cast iron solidifies with a nodularized graphite structure.

6. A method as claimed in claim 1 wherein said cup is coated with said bismuth.

7. A method as claimed in claim 1 wherein a pellet of said bismuth is inserted into said cup.

8. A ceramic test cup having a cavity for receiving, when full, a selected weight of molten cast iron, said cavity containing bismuth in an amount in the range of 0.005–0.025% by weight of said selected weight of molten cast iron.

9. A ceramic test cup as claimed in claim 8 including thermocouple means connectable to temperature indicating means whereby a melt cooling curve may be generated.

10. A ceramic test cup as claimed in claim 9 wherein said temperature indicating means includes a temperature recording means.

11. Apparatus for measuring a eutectic recalescence temperature (TER) and a eutectic undercooling temperature (TEU) in a cooling cast iron melt which has been treated with a nodularizing agent, comprising: test cup means having a cavity for receiving, when full, a selected weight of liquid cast iron; said cavity containing bismuth in an amount in the range of 0.005–0.025% by weight of said selected weight of liquid cast iron; thermocouple means; and means connected to said thermocouple means to read and record temperature in said cooling cast iron melt at selected intervals of time so as to produce a cooling rate curve for said cast iron melt, including said TER and TEU, the difference between which provides a measure of nodularity in said cast iron melt upon solidification.

* * * * *